(12) United States Patent
Lee et al.

(10) Patent No.: US 7,407,913 B2
(45) Date of Patent: *Aug. 5, 2008

(54) PROCESS FOR THE CONTROL OF WEEDS

(75) Inventors: Bruce Lee, Bad Krozingen (DE); Andreas Zoschke, Weil am Rhein (DE); Hans Peter Lutz, Basel (CH)

(73) Assignee: Syngenta Crop Protection, Inc., Greensboro, NC (US)

( * ) Notice: Subject to any disclaimer, the term of this patent is extended or adjusted under 35 U.S.C. 154(b) by 340 days.

This patent is subject to a terminal disclaimer.

(21) Appl. No.: 10/609,084

(22) Filed: Jun. 27, 2003

(65) Prior Publication Data

US 2004/0097373 A1  May 20, 2004

Related U.S. Application Data

(63) Continuation of application No. 09/795,073, filed on Feb. 26, 2001, now Pat. No. 6,586,367, which is a continuation of application No. 09/242,658, filed as application No. PCT/EP97/04795 on Sep. 3, 1997, now abandoned.

(30) Foreign Application Priority Data

Sep. 5, 1996  (CH) ..................................... 2202/96

(51) Int. Cl.
*A01N 57/00* (2006.01)
(52) U.S. Cl. ...................................... 504/127; 504/128
(58) Field of Classification Search ................. 504/127, 504/128
See application file for complete search history.

(56) References Cited

U.S. PATENT DOCUMENTS

| | | | |
|---|---|---|---|
| 4,671,819 A | 6/1987 | Meyer et al. | |
| 4,769,061 A | 9/1988 | Comai | |
| 4,816,063 A | 3/1989 | Yamaguchi et al. | |
| 4,853,026 A | 8/1989 | Frisch et al. | |
| 5,002,606 A | 3/1991 | Moser et al. | |
| 5,071,464 A | 12/1991 | Bauer et al. | |
| 5,094,945 A | 3/1992 | Comai | |
| 5,152,823 A | 10/1992 | Albrecht et al. | |
| 5,183,492 A | 2/1993 | Suchy et al. | |
| 5,209,771 A | 5/1993 | Meyer | |
| 5,221,314 A * | 6/1993 | Watson et al. | 504/117 |
| 5,457,085 A | 10/1995 | Seckinger et al. | |
| 5,599,769 A | 2/1997 | Hacker et al. | |
| 6,046,134 A * | 4/2000 | De Gennaro et al. | 504/133 |

FOREIGN PATENT DOCUMENTS

| | | |
|---|---|---|
| AU | 704539 | 1/1997 |
| AU | 710367 | 4/1997 |
| CA | 1291344 | 10/1991 |
| CA | 1337597 | 11/1995 |
| DE | 2839087 | 3/1980 |
| DE | 3615711 | 9/1987 |
| EP | 0076470 | 9/1982 |
| EP | 0218571 | 4/1987 |

(Continued)

OTHER PUBLICATIONS

Flint (Weed Science, 1989, vol. 37, 12-18).*

(Continued)

*Primary Examiner*—Sreeni Padmanabhan
*Assistant Examiner*—Uma Ramachandran
(74) *Attorney, Agent, or Firm*—Thomas Hamilton

(57) ABSTRACT

Undesired plant growth in cultivations of useful plants which are resistant to phopho-herbicides, may be controlled with herbicidal compositions, which contain, in addition to the usual inert formulation assistants, a phospho-herbicide and a synergistic amount of at least one further herbicide selected from the group comprising prosulfuron, primisulfuron, dicamba, pyridate, dimethenamide and its S-enantiomer, metolachlor and its S-enantiomer, fluometuron, propaquizafop, atrazine, clodinafop, norflurazone, ametryn, terbutylazine, simazine, prometryn, NOA-402989, as well as the compounds of formulae

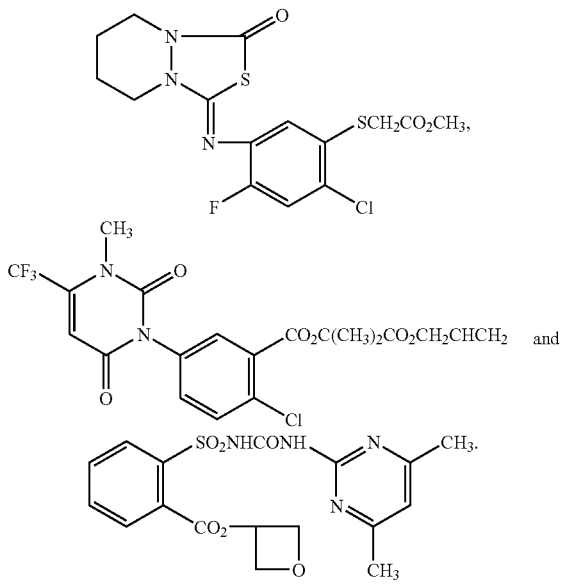

28 Claims, No Drawings

FOREIGN PATENT DOCUMENTS

| | | |
|---|---|---|
| EP | 0 252 897 A2 | 1/1988 |
| EP | 257542 | 3/1988 |
| EP | 0268574 | 5/1988 |
| EP | 357553 | 8/1989 |
| EP | 0343142 | 11/1989 |
| EP | 378985 | 12/1989 |
| EP | 0 354 201 A2 | 2/1990 |
| EP | 0 387 165 A1 | 9/1990 |
| EP | 409815 | 1/1991 |
| EP | 441764 | 1/1991 |
| EP | 462585 | 12/1991 |
| EP | 499798 | 1/1992 |
| EP | 475392 | 3/1992 |
| EP | 496701 | 7/1992 |
| EP | 614606 | 2/1994 |
| GB | 2 233 229 | 1/1991 |
| WO | 89/04607 | 6/1989 |
| WO | 92/08353 | 5/1992 |
| WO | 93/21772 | 11/1993 |
| WO | 9419949 | 9/1994 |
| WO | 96/25043 | 8/1996 |
| WO | 96/32013 | 10/1996 |
| WO | 96/34528 | 11/1996 |
| WO | 97/24930 | 7/1997 |
| WO | 97/34484 | 9/1997 |

OTHER PUBLICATIONS

Waters, S. "Glyphosate-tolerant crops for the future: Development, risks and benefits", Brighton Crop Protection Conference-Weeds (1991), 165-70.

Moshier, L.J. and Russ, O.G. "Response of Honeyvine Milkweed to Herbicides", North Central Weed Control Conference (1978) 33, 108.

Walker, S.R., Hargreaves, P.A. and Noble, R.M. "Potential for Herbicide Residues to Contaminate Australian Soils and Waters", Herbicide-Resistant Crops and Pastures. Aust. Farming Syst. Proc. Workshop (1995), 191-199.

Yortt, M. L. "Control of Annual and Perennial Weeds in Maize Established by Conventional and Conservation Tillage Practices", Proc. New Zealand Weed and Pest Control Conference (1982) 35th, pp. 215-218.

Research Disclosure No. 37242, published Apr. 1995.

Myers, M.G. and Harvey, R.G., "Triazine-Resistant Common Lambsquarters Control in Field Corn", Weed Technology 7, (1993) pp. 884-889.

Moshier, L.J., "Response of Honeyvine Milkweed to Herbicide Applications", Weed Science (1980) 28(6), 722-724.

Roundup Ultra herbicide booklet—21137T1-2/53.

Roundup Ultra herbicide booklet—21137U2-2/53.

Roundup Ultra herbicide booklet—21001S1-28/53.

Material Safety Data Sheet filed with the United States Occupational Safety and Health Administration for Dual Herbicide.

Material Safety Data Sheet filed with the United States Occupational Safety and Health Administration of Solicam DF Herbicide.

"The Pesticide Manual, 10th Edition" (1994). Entries 369, 476, 593, 569, 202, 605, 232, 332, 582, 36, 148, 22, 664, 627, 577.

Moser, H., Rihs, G., Sauter, H.P., and Bohner, B., "Atropisomerism, Chiral Centre and Activity of Metolachlor" Pesticide Chemistry: human welfare and the environment, vol. 1. Synthesis and structure-activity relationships (1983) pp. 315-320.

Australian Weed Control Handbook, Tenth Edition, Inkata Press, Melbourne, 1995, pp. 380-396, 138-142, 127-133, 180-181, 217-230, 233-234 and 397-398.

"Herbicide Handbook", Weed Science Society of America, Seventh Edition, 1994, pp. 149-152.

Herbicides. Chemistry, Degradation, and Mode of Action, vol. 3 (1988), edited by P.C.Kearney and D.D.Kaufman, published by Marcel Dekker, Inc., New York, pp. 338-345 and 374-377.

Harr, J., Seckinger, K., Ummel, E. and Hargett L.T. "SAN 582 H—A new herbicide for weed control in corn and soybeans", Proceedings of the Brighton Crop Protection Conference—Weeds—1991, pp. 87-92.

Charles, G.W., Constable, G.A. and Kennedy, I.R. "Current and future weed control practices in cotton: the potential use of transgenic herbicide resistance" pp. 89-100 in G.D.McLean and G.Evans, (eds) 1995, Herbicide-resistant Crops and Pastures in Australian Farming Systems.

Rasche, E. "Development of glufosinate ammonium tolerant crops and the selective use of the herbicide glufosinate ammonium", pp. 25-33 in G.D.McLean and G.Evans, (eds) 1995, Herbicide-resistant Crops and Pastures in Australian Farming Systems.

Res. Rep. North Cent. Weed Sci. Soc. (52, 266-267, 1995).

Res. Rep. North Cent. Weed Sci. Soc. (52, 426-427, 1995).

Zeitschrift fur Pflanzenkrankheiten und Pflanzenschuts, Sonderheft X, 335-360 (1984).

Research Report North Central Weed Science Society, 169-171 (1994).

Research Report Expert Committee Weeds Eastern Canada (40 Meet., vol. 1, 205-206, 1995).

Research Report Expert Committee Weeds Eastern Canada (40 Meet., vol. 1, 242-243, 1995).

Flint et al., Effects of Gluphosate Combinations with 2,4-D or Dicamba on Field Bindweed (*Convolvulus arvensis*). Weed Science, 37:12-18.

Research Disclosure, Apr. 1995, 271, 37242.

J.M. Lich et al., Interaction of Glyphosate with Postemergence Soybean (Glycine Max) Herbicides, Weed Science 45(1), 12-21 (1997).

Research Disclosure, Mar. 1987, 275, 27546.

P. Hornus, Oleagineux 45 (2), 57-68 (1990).

P. Langeluddeke et al., British Crop Prot. Conf. Weeds, 1985, vol. 3, S. 1047-1052.

P. Westra et al., Field Bindweed (*Convolvulus arvensis*) Control with Various Herbicide Combinations, Weed Technology 6 (4), 949-955 (1992).

S.M. Brown et al., Weed Control Programs for Minimum Tillage Cotton (*Gossypium birsutum*) Weed Science 33(6), 843-847 (1985).

S. Tan et al., Leaching of Bromacil and Norflurazon as Affected by Herbicide Mixture, J. Environ. Qual. 24, 970-972 (1995).

European Opposition No. GVX/P-C6 HESTER OPPO 01 filed Sep. 18, 2004 by Opposer BASF Aktiengesellschaft in opposition to the grant of Patent No. EP-B-930823 / EP Application No. 97 940 156.9 by Proprietor Syngenta Participations AG; Decision issued on Jul. 28, 2006.

Australian Opposition filed by Opponent Monsanto Company on Aug. 21, 2000, in opposition to Australian Patent Application No. 720095, entitled "Process for the Control of Weeds," in the name of Applicant Syngenta Participations AG; Decision issued on Aug. 16, 2005.

Declaratory Judgment Action styled Monsanto Company v. Syngenta Crop Protection, Inc., No. 4-07cv543 (E.D. Mo. filed Mar. 20, 2007).

Chemical Abstracts, vol. 124, abs. No. 79375m.

\* cited by examiner

PROCESS FOR THE CONTROL OF WEEDS

This application is a Continuation of Ser. No. 09/795,073, filed Feb. 26, 2001, now U.S. Pat. No. 6,586,367, which is a Continuation of Ser. No. 09/242,658, filed Feb. 19, 1999 now abandoned, which was filed under 35 USC 371 as a national stage application of PCT/EP97/04795, filed Sep. 3, 1997, the contents of which are herein incorporated by reference.

The present invention relates to a new process for the control of weeds in useful plant cultivations, for example in the cultivation of maize, soya, cotton, rape, beet and sugar cane, which are resistant to phospho-herbicides.

The phospho-herbicides glufosinate and glyphosate are described for example in The Pesticide Manual, Tenth Edition, 1994, Crop Protection Publications, BCPC. In addition, the following herbicides are similarly known: prosulfuron, primisulfuron, dicamba, pyridate, dimethenamide, metolachlor, fluometuron, propaquizafop, atrazine, ametryn, terbutylazine, simazine, clodinafop, norflurazone, as well as prometryn. The S-enantiomer of metolachlor is known from U.S. Pat. No. 5,002,606; the S-enantiomer of dimethenamide from U.S. Pat. No. 5,457,985. The metabolite NOA-402989 is known from the Zeitschrift für Pflanzenkrankheiten und Pflanzenschutz, Sonderheft X, 355-360 (1984) as 3-phenyl-4-hydroxy-6-chloropyridazine. The compound of formula

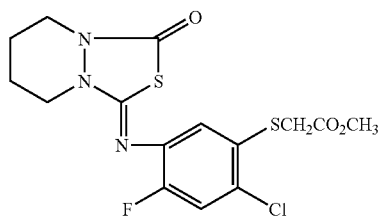

is described for example in U.S. Pat. No. 4,671,819; U.S. Pat. No. 5,183,492 discloses the compound of formula

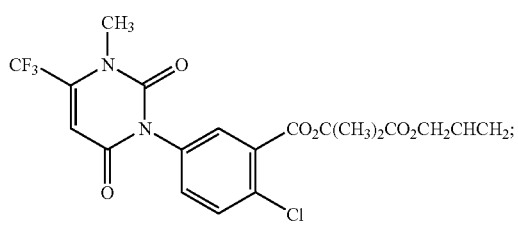

and the compound of formula

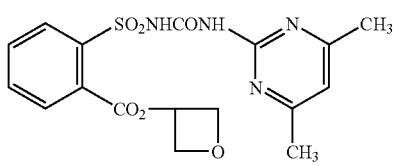

is known from EP-A-496 701.

It has now surprisingly been found that a quantitatively variable combination of phospho-herbicides selected from the group comprising glufosinate and glyphosate with at least one of the above-listed other herbicides exhibits a synergistic effect which is capable of controlling the majority of weeds occurring preferably in useful plant cultivations that are resistant to glufosinate or glyphosate, both in pre-emergence and in post-emergence, without significantly damaging the useful plants.

Therefore, according to the present invention, a new process is proposed for the control of weeds in the cultivation of useful plants that are resistant to phopho-herbicides, the process being characterised in that a herbicidally effective amount of a composition containing, in addition to the usual inert formulation assistants, a phospho-herbicide selected from the group comprising glufosinate and glyphosate, a synergistic amount of at least one further herbicide selected from the group comprising prosulfuron, primisulfuron, dicamba, pyridate, dimethenamide and its S-enantiomer, metolachlor and its S-enantiomer, fluometuron, propaquizafop, atrazine, clodinafop, norflurazone, ametryn, terbutylazine, simazine, prometryn, NOA-402989, as well as the compounds of formulae

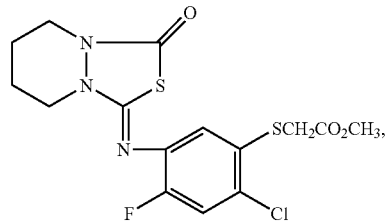

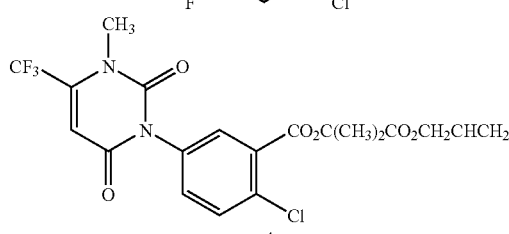

and

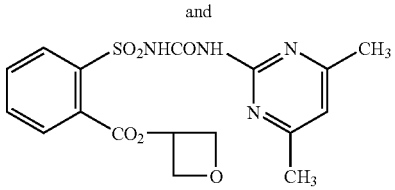

is allowed to take effect on the cultivated plant or its habitat, with the provision that compositions containing glufosinate and metolachlor, glufosinate and atrazine, glufosinate and metolachlor and atrazine, as well as glutosinate and atrazine and dicamba are not used in glufosinate-resistant maize, and further that compositions containing glyphosate and atrazine are not used in glyphosate-resistant maize, and compositions containing glyphosate and metalochlor or glyphosate and dimethenamide are not used in glyphosate-resistant soya.

It is highly surprising that the combination of a phospho-herbicide such as glufosinate or glyphosate with at least one of the above-mentioned further herbicides surpasses the additional effect to be expected in principle on the weeds to be controlled, and thus extends the limits of activity of both active ingredients in particular in two different respects.

On the one hand, the application amounts of the individual compounds applied are reduced, whilst maintaining a good level of activity. On the other hand, the composition used according to the invention still achieves a high rate of weed control where the individual substances have become no longer agronomically useful in small application amounts. The consequence of this is a considerable widening of the weed spectrum and an additional increase in selectivity for useful plant cultivations, which is necessary and desired in the case of an unintentional overdose of active ingredient. In addition, the composition according to the invention allows greater flexibility of subsequent cultivations whilst maintaining the outstanding control of weeds in useful plants.

The herbicide mixture used according to the invention may be used on glufosinate- or glyphosate-resistant useful plants, especially maize, cotton, rape, sugar beet, sugar cane and soya, against a large number of agronomically important weeds, such as Stellaria, Nasturtium, Agrostis, Digitaria, Avena, Setaria, Sinapis, Lolium, Solanum, Phaseolus, Echinochloa, Scirpus, Monochoria, Sagittaria, Bromus, Alopecurus, Sorghum halepense, Rottboellia, Cyperus, Abutilon, Sida, Xanthium, Amaranthus, Chenopodium, Ipomoea, Chrysanthemum, Galium, Viola and Veronica. It may also be used for non-selective weed control and for all application methods that are usual in agriculture, e.g. pre-emergent application, post-emergent application and seed disinfecting.

Useful plant cultivations which are tolerant towards the herbicide glufosinate or glyphosate are preferably produced with the assistance of biotechnological methods. The assistance of biotechnological processes can be restricted to the usage of cell-biological selection processes, which are carried out in such cases preferably on cell or callus cultures that are capable of regeneration, so as to finally develop glutosinate- or glyphosate-tolerant plants. However, since precise knowledge is available about the mechanism of activity of these herbicides, gene technology may also be employed.

Resistance towards glufosinate may be essentially attained by two different experimental setups. On the one hand, the herbicide target which in the case of glufosinate is represented by the enzyme glutamine synthetase may be selected as the point of attack for the development of resistance. On the other hand, the herbicidally active substance itself may serve as the starting point for the development of resistance. For example, glufosinate tolerance may be effected through the transgenic expression of an enzyme which converts glutosinate into a physiologically inactive form.

The first set-up makes use of the knowledge of the site of action or the point of attack of glufosinate, namely the enzyme glutamine synthetase. The desired tolerance may thus be effected by over-expression of the enzyme in plants or preferably by transgenic expression of variants of the enzyme which are tolerant to the effect of glufosinate.

Glufosinate-tolerant plants are thus produced e.g. by amplifying the herbicide target in the plant. Such gene amplification is achieved for example by exposing plant cell cultures to selection pressure, and further cultivating the resistant variants or strains obtainable in this way and regenerating them into whole plants. The said resistant cell strains may also be fused with an appropriate receptor cell line in the manner of a protoplast fusion, and regenerated into whole plants. Alternatively, the desired gene amplification may also be attained with the assistance of genetic engineering, whereby the number of wild type genes in the plant genome of sensitive plants is increased by inserting further wild type gene replications. The source of wild type genes which encode the enzyme glutamine synthetase may be both procaryotes and especially eucaryotes. The eucaryotes are presented in particular by plant sources, e.g. various species of potato (Solanum tuberosum), tomato (Lycopersicon esculentum), pepper (Capsicum annumm), tobacco (Nicotiana tabacum), brassica, especially Brassica napus, various leguminosae e.g. alfalfa (Medicago sativa), clover (Trifolium sp.), soya (Glycine max), various species of bean (Phaseolus sp., Vici sp, Vigna sp.), peas (Pisum sativum), various root crops, e.g. Beta vulgaris, carrots (Daucus carota), sweet potatoes (Ipomoea batatus) as well as others, for example Arabidopsis thaliana.

Glufosinate-tolerant plants may also be produced by inserting genes that encode a mutated glutamine synthetase enzyme which is resistant towards the inhibitory activity of glufosinate. As in the case of the above-mentioned wild type genes, these are cloned into expression cassettes developed especially for plants, and are transformed into the desired host plant. Appropriate expression signals (essentially promoter and termination signals, as well as signal and enhancer sequences), which are recognised by the plant cell and lead to effective expression of the respective gene products in the transformed plant, and which may be employed within the said expression cassettes, are most familiar to the person skilled in the art.

The processes for the production of such glufosinate-tolerant plants are described in detail in international applications having publication nos. WO 86/02097 and WO 87/05627, and reference thereto is incorporated in the present application.

The recombinant DNA molecules thus produced may be inserted into the plant by means of various transformation processes known to the person skilled in the art, and brought to expression there. The person skilled in the art is aware that the choice of an appropriate method is dependent in particular on the species of plant respectively selected. Suitable transformation processes include for example micro-injection (Crossway et al., Bio Techniques 4:320-334 (1986)), electroporation (Riggs et al, Proc. Natl. Acad. Sci. USA 83:5602-5606 (1986), Agrobacterium-mediated transformation (Hinchee et al., Biotechnology 6:915-921 (1988)), direct gene transfer processes (Paszkowski et al., EMBO J. 3:2717-2722 (1984)), as well as ballistic processes using microprojectiles ('ballistic particle acceleration') [see for example Sanford et al., U.S. Pat. No. 4,945,050; and McCabe et al., Biotechnology 6:923-926 (1988)].

One especially preferred process for inserting recombinant DNA molecules into maize plants is described in the international application having publication no. WO 93/07278 and EP-A 0 292 435, and reference thereto is incorporated in the present application.

As has already been mentioned, glufosinate-tolerant plants may also be produced by aiming at the herbicidally active compound as such and inactivating it. Thus, for example, genes may be isolated from the streptomycetes strains S. hygrocopicus and S. viridochromogenes, which were selected for bialaphos or phosphinotricine (=glufosinate) resistance, and these genes encode an enzyme which acetylates the free $NH_2$ group of glufosinate and thus transforms it to a non-herbicidally active compound. The transgenic expression of these phosphinothricine acetyl-transferase genes in useful plants is capable of eliminating the locking-up of the nitrogen metabolism in the plant by the glufosinate and leads to glufosinate tolerance of said plants.

The efficiency of expression of recombinant DNA molecules of bacterial origin in plants may be controlled by the production of synthetic genes. For example, genes of streptomycetes normally possess a very high G/C proportion of up to 70%, which may be reduced to the usual amount for plant genes of ca. 50% by resynthesis of the gene, whilst taking into account the usual codon usage of plants.

The efficiency of expression may normally be further increased by optimising the codon usage in such a way that only those codons that are most preferred in the respective target plant, for example maize, are used for gene resynthesis.

Further details relating to the construction of synthetic genes which have been optimised for expression in maize may be found e.g. in the international application having publication no. WO 93/07278.

The glufosinate-tolerant plants obtainable in this way may then be propagated, i.e. produced, by means of conventional cultivation methods, whereby the glufosinate tolerance is passed on to subsequent generations by transmission.

The processes for the production of such glufosinate-tolerant plants are described in detail in the European applications having the publication nos. EP-A 242 236, EP-A 242 246, EP-A 257 542 and EP-A 275 957 and reference thereto is incorporated in the present application.

Glyphosate-resistant plants may be produced in a similar manner, whereby a gene is used which codes for a glyphosate-tolerant EPSP synthase, as is described in EP-A-115673 and EP-A-409815.

By the expression plants or useful plant cultivations that are resistant to the herbicide glufosinate or glyphosate, as is employed in the present application, are understood also plants or useful plant cultivations which are resistant to those herbicides that are metabolised in the plant or in the useful plant cultivations to glufosinate, as is the case for example when using bilanafos, or to glyphosate.

Maize which is resistant to glufosinate was treated with a tank mixture containing glufosinate and atrazine according to Res. Rep. North Cent. Weed Sci. Soc., 51, 169-170, 1994. Further tank mixtures for use in glufosinate-resistant maize are described in Res. Rep. Expert Comm. Weeds East Can., 1,242-243,1995 and Res. Rep. Expert Comm. Weeds East Can., 1, 205-206, 1995. The treatment of glyphosate-resistant maize or glyphosate-resistant soya with mixtures of glyphosate and atrazine, metolachlor or dimethenamide is described in Abstr. Meet. Weed Sci. Soc. Am. 37, 87, 1997, Res. Rep. North Cent. Weed Sci. Soc., 52, 426-427, 1995 and Res. Rep. North Cent. Weed Sci. Soc., 52, 266-267, 1995.

The active ingredient combination used according to the invention contains glufosinate or glyphosate and at least one of the other herbicides in any ratio of the mixture, normally with an excess of one component over the other. Preferred ratios between glufosinate or glyphosate and the components in the mixture lies between 1:100 and 1:0.001.

A preferred process according to the present invention is characterised in that a herbicidally effective amount of a composition containing, in addition to the usual inert formulation assistants, glufosinate and a synergistic amount of at least one further herbicide selected from the group comprising prosulfuron, primisulfuron, dicamba, pyridate, dimethenamide, metolachlor and its S-enantiomer, fluometuron, propaquizafop, atrazine, ametryn, terbutylazine, simazine, prometryn, as well as the compounds of formulae

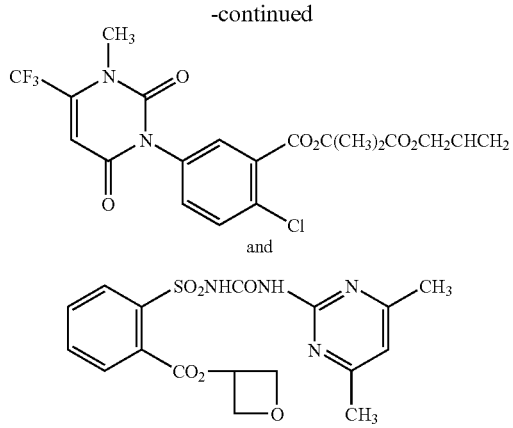

-continued is allowed to take effect on the cultivated plant or its habitat.

Mixtures that have proved to be especially effective when the useful plant cultivation relates to maize, which is resistant to glufosinate and/or glyphosate, are combinations of glufosinate or glyphosate with a synergistic amount of at least one further herbicide selected from the group comprising prosulfuron, primisulfuron, dicamba, pyridate, dimethenamide as well as its S-enantiomer, metolachlor as well as its S-enantiomer, atrazine, NOA-402989, ametryn, terbutylazine, simazine, prometryn, as well as the compounds of formulae

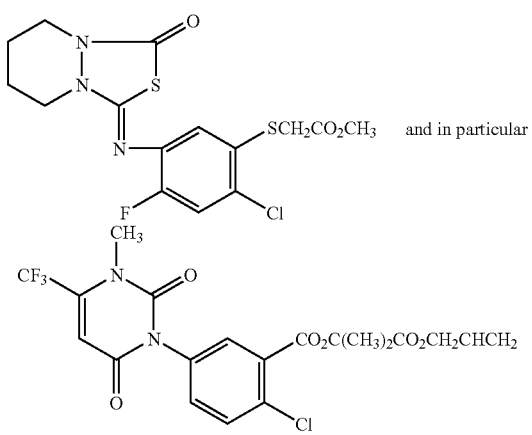

or combinations of glufosinate with a synergistic amount of at least one further herbicide selected from the group comprising prosulfuron, primisulfuron, dicamba, pyridate, dimethenamide, metolachlor as well as its S-enantiomer, atrazine, ametryn, terbutylazine, simazine, prometryn, as well as the compounds of formulae

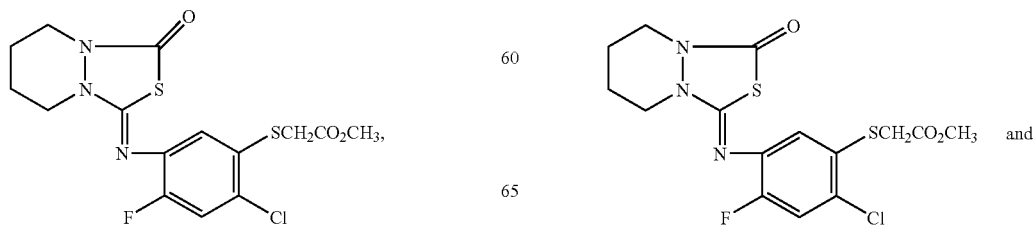

-continued

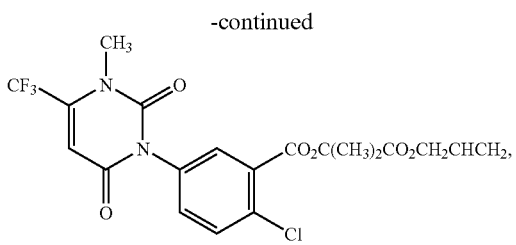

When the useful plant cultivation relates to soya, which is resistant to glufosinate and/or glyphosate, it is preferable to use a composition which contains glufosinate or glyphosate and a synergistic amount of at least one further herbicide selected from the group comprising metolachlor as well as its S-enantiomer and the compounds of formula

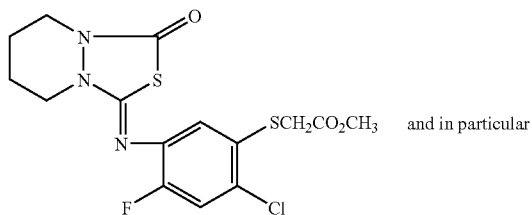 and in particular

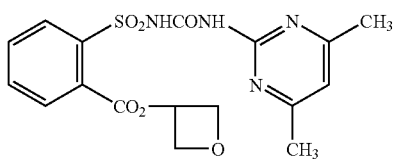

or a composition which contains glufosinate and at least one further herbicide selected from the group comprising metolachlor as well as its S-enantiomer and the compounds of formulae

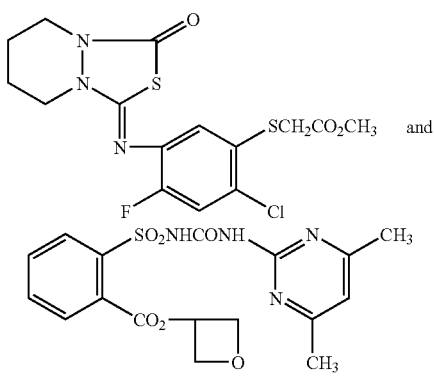

In cotton cultivations, which are resistant to glufosinate and/or glyphosate, a composition is preferably employed which contains glufosinate or glyphosate and a synergistic amount of fluometuron, or which contains glufosinate and a synergistic amount of fluometuron.

In rape or beet cultivations, which are resistant to glufosinate and/or glyphosate, a composition is preferably selected which contains glufosinate or glyphosate and a synergistic amount of propaquizafop, or which contains glufosinate and a synergistic amount of propaquizafop.

When the useful plant cultivation concerned is sugar cane, which is resistant to glufosinate and/or glyphosate, it is preferable to use a composition which contains glufosinate or glyphosate and a synergistic amount of ametryn, or a composition containing glufosinate and a synergistic amount of ametryn.

The amount applied may vary within a wide range, and depends on the nature of the soil, the type of application (pre- or post-emergent; seed disinfecting; usage in the seed drill; no tillage application etc.), the plant cultivated, the weed to be controlled, the prevalent climatic conditions and other factors determined by the type of application, time of application and target cultivation. In general, the active ingredient mixture used according to the invention may be used at an application rate of 0.3 to 4.0 kg active ingredient mixture per hectare.

In the composition used according to the invention, glufosinate or glyphosate is preferably present in a weight ratio of 1:10 to 1000:1 in relation to the other herbicide(s).

The herbicidal compositions which contain, in addition to the usual inert formulation assistants, glufosinate and a synergistic amount of at least one further herbicide selected from the group comprising prosulfuron, primisulfuron, pyridate, dimethenamide and its S-enantiomer, the S-enantiomer of metolachlor, fluometuron, propaquizafop, clodinafop, norflurazone, ametryn, terbutylazine, simazine, prometryn, NOA-402989, as well as the compounds of formulae

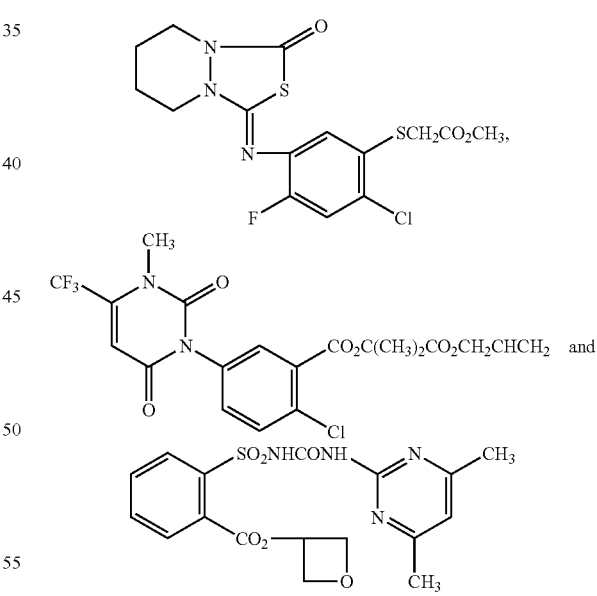

as well as the herbicidal compositions which contain, in addition to the usual inert formulation assistants, glyphosate and a synergistic amount of at least one further herbicide selected from the group comprising prosulfuron, primisulfuron, dicamba, pyridate, the S-enantiomer of dimethenamide, the S-enantiomer of metolachlor, fluometuron, propaquizafop, clodinafop, norflurazone, ametryn, terbutylazine, simazine, prometryn, NOA-402989, as well as the compounds of formulae

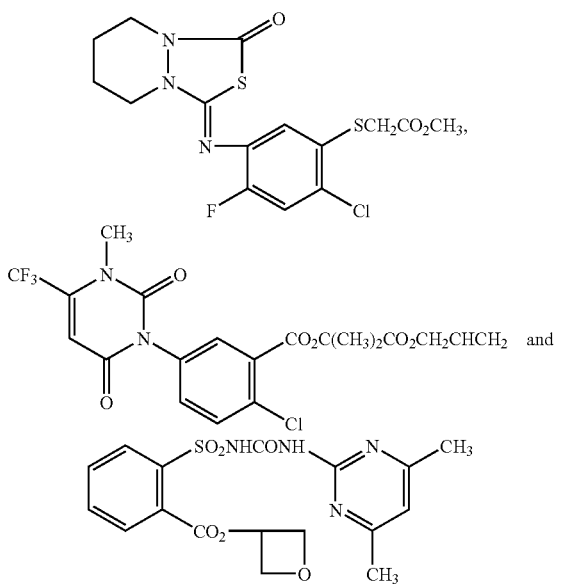

are new and form a further object of the present invention.

Both glufosinate and/or glyphosate and the other herbicides may be used in unchanged form, i.e. as they occur during synthesis, but they are preferably processed in conventional manner with the assistants which are customary in formulation technology, such as solvents, solid carriers or surfactants, e.g. into emulsifiable concentrates, directly sprayable or diluable solutions, spray powders, soluble powders, dusting compositions, granulates or micro-capsules. The application processes such as spraying, atomizing, dusting, sprinkling, dispersing or pouring are selected according to the aims strived for and the given conditions, in the same way as for the type of composition.

The formulations, i.e. the compositions, preparations or compositions containing the active ingredient glufosinate or glyphosate and the other herbicides as well as optionally one or several solid or liquid formulating assistants, are produced in a manner known per se, e.g. by intimately mixing and/or grinding the active ingredients with the formulating assistants such as solvents or solid carriers. In addition, surface-active compounds (surfactants) may be used when producing the formulations.

The solvents in question may be: aromatic hydrocarbons, preferably fractions $C_8$ to $C_{12}$, such as xylene mixtures or substituted naphthalenes, phthalic acid esters such as dibutyl or dioctyl phthalate, aliphatic hydrocarbons such as cyclohexane or paraffins, alcohols and glycols, as well as the ethers and esters thereof, such as ethanol, ethylene glycol, ethylene glycol monomethyl- or -ethyl-ether, ketones such as cyclohexanone, strongly polar solvents such as N-methyl-2-pyrrolidone, dimethyl sulphoxide or N,N-dimethylformamide, as well as optionally epoxidated vegetable oils such as epoxidated coconut oil or soyabean oil; or water.

The solid carriers employed e.g. for dusting compositions and dispersible powders are normally natural mineral powders, such as calcite, talc, kaolin, montmorillonite or attapulgite. To improve the physical properties of the formulation, highly disperse silicic acid or highly disperse absorbent polymerisates may also be added. The granular, adsorptive granulate carriers employed may be porous types such as pumice, brick fragments, sepiolite or bentonite, and the non-absorbent carrier materials are e.g. calcite or sand. Moreover, a number of pregranulated materials of inorganic or organic nature may also be used, especially dolomite or pulverized plant residue.

Depending on the type of active ingredient to be formulated, the surface-active compounds may be non-ionic, cationic and/or anionic surfactants and surfactant mixtures having good emulsifying, dispersing and wetting properties.

Appropriate anionic surfactants may be both so-called water-soluble soaps and water-soluble synthetic surface-active compounds.

Soaps which may be mentioned are the alkali salts, alkaline earth salts or optionally substituted ammonium salts of higher fatty acids ($C_{10}$-$C_{22}$), e.g. the Na or K salts of oleic or stearic acid, or of natural fatty acid mixtures, which may be obtained e.g. from coconut oil or tallow oil. Furthermore, the fatty acid methyl-taurine salts may also be mentioned.

More frequently however, so-called synthetic surfactants are used, especially fat alcohol sulphonates, fat alcohol sulphates, sulphonated benzimidazole derivatives or alkylaryl sulphonates.

The fat alcohol sulphonates or sulphates are normally present as alkali salts, alkaline earth salts or optionally substituted ammonium salts and have an alkyl radical with 8 to 22 C-atoms, whereby alkyl also includes the alkyl moiety of acyl radicals, e.g. the Na or Ca salt of lignin sulphonic acid, of dodecylsulphuric acid ester or of a fat alcohol sulphate mixture produced from natural fatty acids. This also includes the salts of sulphuric acid esters and sulphonic acids of fat alcohol/ethylene oxide adducts. The sulphonated benzimidazole derivatives preferably contain 2 sulphonic acid groups and one fatty acid radical with 8-22 carbon atoms. Alkylaryl sulphonates are e.g. the Na, Ca or triethanolamine salts of dodecylbenzenesulphonic acid, of dibutylnaphthalene-sulphonic acid or of a naphthalene-sulphonic acid/formaldehyde condensation product.

The corresponding phosphates such as the salts of the phosphoric acid ester of a p-nonyl-phenol-(4-14)-ethylene oxide adduct or phospholipids may also be considered.

The non-ionic surfactants may be primarily polyglycol ether derivatives of aliphatic or cycloaliphatic alcohols, saturated or unsaturated fatty acids and alkylphenols, which may contain 3 to 30 glycol ether groups and 8 to 20 carbon atoms in the (aliphatic) hydrocarbon radical and 6 to 18 carbon atoms in the alkyl radical of the alkylphenols.

Further appropriate non-ionic surfactants are the water-soluble polyethylene oxide adducts to polypropylene glycol, ethylenediamino-polypropylene glycol and alkyl-polypropylene glycol, containing 20 to 250 ethylene glycol ether groups and 10 to 100 propylene glycol ether groups, with 1 to 10 carbon atoms in the alkyl chain. The said compounds normally contain 1 to 5 ethylene glycol units per propylene glycol unit.

Examples of non-ionic surfactants which may be mentioned are nonylphenol polyethoxy ethanols, castor oil polyglycol ether, polypropylene-polyethylene oxide adducts, tributylphenoxy-polyethoxy ethanol, polyethylene glycol and octylphenoxy-polyethoxy ethanol.

Fatty acid esters of polyoxyethylene sorbitan, such as polyoxyethylene sorbitan trioleate, may also be considered.

The cationic surfactants in question are in particular quaternary ammonium salts, which contain as the N-substituents at least one alkyl radical with 8 to 22 C-atoms and as further substituents low, optionally halogenated alkyl, benzyl or low hydroxyalkyl radicals. The salts are preferably present as halides, methyl sulphates or ethyl sulphates, e.g. stearyl trimethylammonium chloride or benzyl-di-(2-chloroethyl)-ethylammonium bromide.

The surfactants which are customary in formulation techniques and which may also be used in the compositions according to the invention are described inter alia in "Mc Cutcheon's Detergents and Emulsifiers Annual" MC Publishing Corp., Ridgewood N.J., 1981, Stache, H., "Tensid-Taschenbuch", Carl Hanser Verlag, Munich/Vienna, 1981 and M. and J. Ash, "Encyclopedia of Surfactants", Vol I-III, Chemical Publishing Co., New York, 1980-81.

The herbicide formulations normally contain 0.1 to 99% by weight, especially 0.1 to 95% by weight of active ingredient mixture, 1 to 99.9% by weight of a solid or liquid formulation excipient and 0 to 25% by weight, especially 0.1 to 25% by weight of a surfactant.

While concentrated compositions are usually preferred as a commercial product, the final user normally uses diluted compositions.

The compositions may also contain further additives such as stabilizers, e.g. optionally epoxidated plant oils (epoxidated coconut oil, rapeseed oil or soyabean oil), defoamers, e.g. silicone oil, preservatives, viscosity regulators, binding compositions, adhesives, as well as fertilizers or other active ingredients.

Preferred formulations are made up in particular as follows:

(%=percent by weight)

| Emulsifiable concentrates: | |
| --- | --- |
| active ingredient mixture: | 1 to 90%, preferably 5 to 20% |
| surface-active composition: | 1 to 30%, preferably 10 to 20% |
| liquid carrier: | 5 to 94%, preferably 70 to 85% |
| Dusts: | |
| active ingredient mixture: | 0.1 to 10%, preferably 0.1 to 5% |
| solid carrier: | 99.9 to 90%, preferably 99.9 to 99c% |
| Suspension concentrates: | |
| active ingredient mixture: | 5 to 75%, preferably 10 to 50% |
| water: | 94 to 24%, preferably 88 to 30% |
| surface-active composition: | 1 to 40%, preferably 2 to 30% |
| Wettable powders: | |
| active ingredient mixture: | 0.5 to 90%, preferably 1 to 80% |
| surface-active composition: | 0.5 to 20%, preferably 1 to 15% |
| solid carrier material: | 5 to 95%, preferably 15 to 90% |
| Granulates: | |
| active ingredient mixture: | 0.1 to 30%, preferably 0.1 to 15% |
| solid carrier material: | 99.5 to 70%, preferably 97 to 85% |

The following examples illustrate the invention further without restricting it.

FORMULATION EXAMPLES FOR THE ACTIVE INGREDIENT MIXTURES USED ACCORDING TO THE INVENTION (%=percent by weight)

| F1. Emulsion concentrates | a) | b) | c) | d) |
| --- | --- | --- | --- | --- |
| active ingredient mixture | 5% | 10% | 25% | 50% |
| Ca dodecylbenzene sulphonate | 6% | 8% | 6% | 8% |
| castor oil polyglycol ether (36 mols EO) | 4% | — | 4% | 4% |
| octylphenol polyglycol ether (7-8 mols EO) | — | 4% | — | 2% |
| cyclohexanone | — | — | 10% | 20% |
| arom. hydrocarbon mixture $C_9$-$C_{12}$ | 85% | 78% | 55% | 16% |

Emulsions of each desired concentration may be produced from such concentrates by dilution with water.

| F2. Solutions | a) | b) | c) | d) |
| --- | --- | --- | --- | --- |
| active ingredient mixture | 5% | 10% | 50% | 90% |
| 1-methoxy-3-(3-methoxy-propoxy)-propane | — | 20% | 20% | — |
| polyethylene glycol MW 400 | 20% | 10% | — | — |
| N-methyl-2-pyrrolidone | — | — | 30% | 10% |
| arom. hydrocarbon mixture $C_9$-$C_{12}$ | 75% | 60% | — | — |

The solutions are suitable for application in the form of the smallest droplets.

| F3. Spray powder | a) | b) | c) | d) |
| --- | --- | --- | --- | --- |
| active ingredient mixture | 5% | 25% | 50% | 80% |
| Na lignin sulphonate | 4% | — | 3% | — |
| Na lauryl sulphate | 2% | 3% | — | 4% |
| Na diisobutyl naphthalene sulphonate | — | 6% | 5% | 6% |
| octylphenyl polyglycol ether (7-8 mols EO) | — | 1% | 2% | — |
| highly disperse silicic acid | 1% | 3% | 5% | 10% |
| kaolin | 88% | 62% | 35% | — |

The active ingredient is mixed well with the additional materials and ground well in an appropriate mill. Spray powders are obtained, which may be diluted with water to suspensions of any desired concentration.

| F4. Coated granules | a) | b) | c) |
| --- | --- | --- | --- |
| active ingredient mixture | 0.1% | 5% | 15% |
| highly disperse silicic acid | 0.9% | 2% | 2% |
| inorg. carrier material (Ø 0.1-1 mm) such as $CaCO_3$ or $SiO_2$ | 99.0% | 93% | 83% |

The active ingredient is dissolved in methylene chloride, sprayed onto the carrier and the solvent subsequently evaporated in a vacuum.

| F5. Coated granules | a) | b) | c) |
| --- | --- | --- | --- |
| active ingredient mixture | 0.1% | 5% | 15% |
| polyethylene glycol MW 200 | 1.0% | 2% | 3% |
| highly disperse silicic acid | 0.9% | 1% | 2% |
| inorg. carrier material (Ø 0.1-1 mm) such as $CaCO_3$ or $SiO_2$ | 98.0% | 92% | 80% |

The finely ground active ingredient is evenly applied in a mixer onto the carrier material which has been moistened with polyethylene glycol. In this way, dust-free coated granules are obtained.

| F6. Extrusion granules | a) | b) | c) | d) |
|---|---|---|---|---|
| active ingredient mixture | 0.1% | 3% | 5% | 15% |
| Na lignin sulphonate | 1.5% | 2% | 3% | 4% |
| carboxymethyl cellulose | 1.4% | 2% | 2% | 2% |
| kaolin | 97.0% | 93% | 90% | 79% |

The active ingredient is mixed with the additives, ground and moistened with water. This mixture is extruded and subsequently dried in a current of air.

| F7. Dusting composition | a) | b) | c) |
|---|---|---|---|
| active ingredient mixture | 0.1% | 1% | 5% |
| talcum | 39.9% | 49% | 35% |
| kaolin | 60.0% | 50% | 60% |

By mixing the active ingredient with the carrier materials and grinding in an appropriate mill, a dusting composition is obtained which is ready for use.

| F8. Suspension concentrates | a) | b) | c) | d) |
|---|---|---|---|---|
| active ingredient mixture | 3% | 10% | 25% | 50% |
| ethylene glycol | 5% | 5% | 5% | 5% |
| nonylphenol polyglycol ether (15 mols EO) | — | 1% | 2% | — |
| Na lignin sulphonate | 3% | 3% | 4% | 5% |
| carboxymethyl cellulose | 1% | 1% | 1% | 1% |
| 37% aqueous formaldehyde solution | 0.2% | 0.2% | 0.2% | 0.2% |
| silicone oil emulsion | 0.8% | 0.8% | 0.8% | 0.8% |
| water | 87% | 79% | 62% | 38% |

The finely ground active ingredient is intimately mixed with the additives. In this way, a suspension concentrate is obtained, from which suspensions of any desired concentration may be prepared by dilution with water.

It is often more practical to formulate the active ingredients individually and then, shortly prior to placing in the applicator, to bring them together in water in the desired mixture ratio as a "tank mixture".

BIOLOGICAL EXAMPLES

Test Description (Per-emergent Treatment)

Monocotyledoneous and dicotyledoneous weeds and cultivated plants are sown in small plastic pots in standard soil. Directly after sowing, the test substances are applied in aqueous suspension (500 l water/ha). Subsequently, the test plants are raised under glass under optimum conditions. Evaluation takes place 3 weeks after application using a nine-stage appraisal scale (1=complete damage, 9=no effect). Appraisal marks of 1 to 4 (especially 1 to 3) indicate good to very good herbicide activity. Appraisal marks of 6 to 9 (especially 7 to 9) show good to very good tolerance of cultivated plants.

Test Description (Post-emergent Treatment)

Monocotyledoneous and dicotyledoneous weeds and cultivated plants are raised under glasshouse conditions in small plastic pots in standard soil. Application of the test substances takes place at the 3 to 6 leaf stage of the test plants. The test substances are applied in aqueous suspension (500 l water/ha) at application rates of 5 to 5000 g/ha active substance). Evaluation takes place 3 weeks after application using a nine-stage appraisal scale (1=complete damage, 9=no effect). Appraisal marks of 1 to 4 (especially 1 to 3) indicate good to very good herbicide activity. Appraisal marks of 6 to 9 (especially 7 to 9) show good to very good tolerance of cultivated plants.

In these tests, the herbicide mixtures used according to the invention show good control of the weeds.

The invention claimed is:

1. A process for the control of weeds in cultivations of useful plants which are resistant to glufosinate without significantly damaging the useful plants, comprising applying a herbicidally effective amount of a composition containing glufosinate and at least one further herbicide selected from the group consisting of prosulfuron, primisulfuron, dicamba, pyridate, dimethenamide and its S-enantiomer, metolachlor and its S-enantiomer, propaquizafop, atrazine, and terbuthylazine to the useful plant or its habitat wherein said further herbicide is present in an amount sufficient to provide an increase in selectivity for the useful plants wherein the useful plants would show greater injury if said further herbicide were omitted from said composition, with the provisos that compositions containing glufosinate and metolachlor, glufosinate and atrazine, glufosinate and a mixture of metolachlor and atrazine, or glufosinate and a mixture of atrazine and dicamba are not used in glufosinate-resistant maize.

2. The process according to claim 1, characterised in that the useful plant being cultivated is maize which is resistant to glufosinate and the composition contains glufosinate and at least one further herbicide selected from the group consisting of prosulfuron, primisulfuron, dicamba, pyridate, dimethenamide and its S-enantiomer, the S-enantiomer of metolachlor and terbuthylazine wherein said further herbicide is present in an amount sufficient to provide an increase in selectivity for the useful plants wherein the useful plants would show greater injury if said further herbicide were omitted from said composition.

3. The process according to claim 1, characterised in that the useful plant being cultivated is soya which is resistant to glufosinate, and the composition contains glufosinate and at least one further herbicide selected from the group consisting of dimethenamide and its S-enantiomer and metolachlor and its S-enantiomer.

4. The process according to claim 3, wherein the composition comprises a mixture of glufosinate and dimethenamide.

5. The process according to claim 3, wherein the composition comprises a mixture of glufosinate and the S-enantiomer of dimethenamide.

6. The process according to claim 3, wherein the composition comprises a mixture of glufosinate and metolachlor.

7. The process according to claim 3, wherein the composition comprises a mixture of glufosinate and the S-enantiomer of metolachlor.

8. The process according to claim 1, characterised in that the useful plant being cultivated is rape or beet which are resistant to glufosinate and the composition contains glufosinate and propaquizafop.

9. The process according to claim 1, characterised in that the useful plant cultivations are treated with the said composition at application rates corresponding to 0.3 to 4.0 kg total active ingredient per hectare.

10. The process according to claim 1, wherein the composition comprises a mixture of glufosinate and prosulfuron.

11. The process according to claim 1, wherein the composition comprises a mixture of glufosinate and primisulfuron.

12. The process according to claim 1, wherein the composition comprises a mixture of glufosinate and dicamba.

13. The process according to claim 1, wherein the composition comprises a mixture of glufosinate and pyridate.

14. The process according to claim 1, wherein the composition comprises a mixture of glufosinate and dimethenamide.

15. The process according to claim 1, wherein the composition comprises a mixture of glufosinate and the S-enantiomer of dimethenamide.

16. The process according to claim 1, wherein the composition comprises a mixture of glufosinate and metolachlor.

17. The process according to claim 1, wherein the composition comprises a mixture of glufosinate and the S-enantiomer of metolachlor.

18. The process according to claim 1, wherein the composition comprises a mixture of glufosinate and propaquizafop.

19. The process according to claim 1, wherein the composition comprises a mixture of glufosinate and atrazine.

20. The process according to claim 1, wherein the composition comprises a mixture of glufosinate and terbuthylazine.

21. The process according to claim 2, wherein the composition comprises a mixture of glufosinate and prosulfuron.

22. The process according to claim 2, wherein the composition comprises a mixture of glufosinate and primisulfuron.

23. The process according to claim 2, wherein the composition comprises a mixture of glufosinate and dicamba.

24. The process according to claim 2, wherein the composition comprises a mixture of glufosinate and pyridate.

25. The process according to claim 2, wherein the composition comprises a mixture of glufosinate and dimethenamide.

26. The process according to claim 2, wherein the composition comprises a mixture of glufosinate and the S-enantiomer of dimethenamide.

27. The process according to claim 2, wherein the composition comprises a mixture of glufosinate and the S-enantiomer of metolachlor.

28. The process according to claim 2, wherein the composition comprises a mixture of glufosinate and terbuthylazine.

* * * * *